United States Patent [19] [11] 4,379,931
Plueddemann [45] Apr. 12, 1983

[54] METAL EXTRACTION FROM SOLUTION AND NOVEL COMPOUNDS USED THEREFOR

[75] Inventor: Edwin P. Plueddemann, Midland, Mich.

[73] Assignee: Dow Corning Corporation, Midland, Mich.

[21] Appl. No.: 279,388

[22] Filed: Jul. 1, 1981

[51] Int. Cl.³ .................. C07D 215/12; C07F 7/10
[52] U.S. Cl. .................................. 546/14; 252/430; 252/176; 252/179
[58] Field of Search .............................. 546/14

[56] References Cited
U.S. PATENT DOCUMENTS 3,886,080 5/1975 Schucker et al. ............ 564/14 UX
4,085,108 4/1978 Curran et al. ................ 564/14

FOREIGN PATENT DOCUMENTS 49-48947 12/1974 Japan ........................ 564/14

Primary Examiner—Paul F. Shaver
Attorney, Agent, or Firm—Robert L. McKellar

[57] ABSTRACT

What is disclosed is the preparation of novel silanes, their reaction products on various substrates and the use of the treated substrates to extract metal ions from solution. An example of such a novel compound is

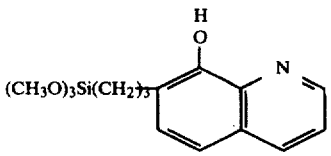

13 Claims, No Drawings

METAL EXTRACTION FROM SOLUTION AND NOVEL COMPOUNDS USED THEREFOR

BACKGROUND OF THE INVENTION

The present invention relates to new and novel silane chelating agents which can be immobilized on inorganic solids and used to chelate metals from solution.

It is well-known in the art to treat inorganic solids with hydrolyzable organosilanes to bond the organosilanes to the inorganic solid surfaces. For example, British Pat. No. 1,530,039 published Oct. 25, 1978 and assigned to the British Petroleum Company Limited, shows the use of polyamines bonded to inorganic solids by the use of an organosilane coupling agent. The organosilane coupling agent is described preferably as alpha-chloropropyl-trimethoxysilane and the polyamine as $N(CH_2CH_2NH_2)_3$. Leyden, et al., Anal. Chem., 47(a), pp. 1612 to 1617, August 1975, shows the use of aminoalkyltrimethoxysilanes as treatments for silica gel to give a silica having aminoalkylsilyl groups on the surface which are subsequently derivatized to the corresponding dithiocarbamate to give chelating groups on the surface of the silica.

Plueddemann, U.S. Pat. No. 4,071,546, issued Jan. 31, 1978, prepared carboxymethyl containing polyaminosiloxanes which were bonded to siliceous supports which were subsequently used as metal chelating agents and Hancock et al., in U.S. Pat. No. 4,203,952, issued May 20, 1980 and assigned to the British Petroleum Company, shows the use of silane coupling agents to bond various amine functional chelating compounds to inorganic solids.

Finally, G. D. Schucker et al., in U.S. Pat. No. 3,886,080, issued May 27, 1975 shows the use of silane coupling agents to immobilize certain chelating agents on inorganic solids. Specifically, the compound 8-hydroxyquinoline is shown as one of the chelating agents that can be bound to inorganic solids by their method.

What has been discovered and disclosed herein is a new and novel means by which to attach the 8-hydroxyquinoline chelating agent to the surface of inorganic solids which results in a new immobilized chelating substance which has durability on the inorganic solid substrate thereby giving the chelating agent extended chelating capacity.

Percolation of dilute heavy metal ion solutions through silylated silica has been used as an analytical method for concentrating the metal ion for estimation by X-ray fluorescence (D. E. Leyden, M. L. Steele and B. B. Jablonski, Anal. Chem. Acta, 100 549 (1978)). In these methods, amine functional silanes were used to bond chelating agents to the silica surface. Materials such as $(CH_3CH_2O)_3Si(CH_2)_3NH_2$ and $(CH_3O)_3Si(CH_2)_3NH(CH_2)_2NH_2$ have been the preferred silylating agents and these materials give almost quantitative yields when used as chelating agents themselves. Capacity for metal ions is proportional to surface area of the filler. These hydrolyzed hydrophilic silanes when deposited under mild conditions on siliceous surfaces are not tightly bonded to the surface through the surface silanols. Siloxane bonds formed between the coupling agent and the siliceous surface are hydrolyzed and if the hydrolyzed hydrophilic silane is a monomer or an uncrosslinked oligomer, the coupling agent is displaced relatively easily from the surface. Crosslinking such monomers or oligomers while on a silica surface, such as by heating, is not a useful method of imparting durability to the treated surface since for the metal ion removal application, the reactivity of the metal ions is reduced or lost.

The hydrophilic diamine group on a silica surface becomes even more hydrophilic in acid solutions such as are used to elute metals from chelate-silylated surfaces.

Among those known useful chelating agents, it is believed that the 8-hydroxyquinoline derivative is probably preferred because it has a higher capacity for chelating more types of metals (see U.S. Pat. No. 3,886,080, Tables I-X).

Further, as it has already been pointed out by Schucker, supra, inorganic solid substrates for immobilization of the chelating agents are preferred over that of organic carriers because the inorganic carriers are biologically stable; they do not tend to swell or shrink with changing conditions of pH and, such compositions can be sterilized without degradation (see Column 2, line 15 et seq. of Schucker).

It would thus appear that it would be desirable to have an 8-hydroxyquinoline chelating agent durably bonded to an inorganic solid so that one could enjoy the combined benefits thereof and overcome prior art disadvantages. The present invention does overcome the disadvantages of the prior art immobilized chelating agents.

It is one object of this invention to provide novel silicon-containing chelating agents which are useful for removing heavy metal ions from solutions.

It is another object of this invention to provide a new process for preparing the novel chelating agents.

It is yet another object of this invention to provide immobilized chelating agents which have durability in use.

These and other objects will become obvious after consideration of the following disclosure and claims.

THE INVENTION

In one aspect, this invention deals with new organosilicon compounds and a method for their preparation. The new organosilicon compounds have the formula

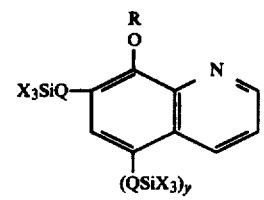

wherein X is an alkoxy radical containing 1-4 carbon atoms; Q is a

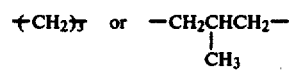

radical; y has a value of 0 or 1; R is hydrogen or an $R'_3Si$— radical wherein R' is $CH_3$— or $CH_3CH_2$—.

It should be noted that the general formula contemplates very few specific compounds since the preparative process used to prepare such compounds requires certain restrictions. For example, Q has been designated as

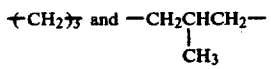

because part of the process requires an allylic rearrangement. Thus, Q precursors are restricted to

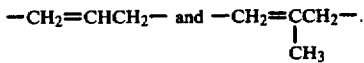

X in the above formula is an alkoxy radical of 1–4 carbon atoms. Thus, X is $CH_3O-$, $CH_3CH_2O-$, $CH_3CH_2CH_2O-$, $CH_3CH_2CH_2CH_2O-$ and their corresponding iso compounds. y in the above formula can be zero or one. When y is zero, the compounds have the general formula

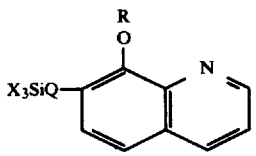

i.e. a monosubstituted product. When y is one, the compounds have the general formula

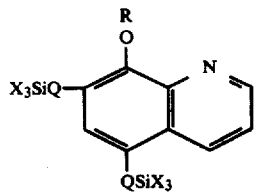

i.e. a bis compound.

R in the above formulae can be hydrogen, that is, the oxy substituent on the benzene ring of the inventive compounds is hydroxy. R can also be the $R'_3Si-$ radical where R' is $CH_3-$ or $CH_3CH_2-$. Thus, the oxy substituent can be a siloxy derivative, that is, $(CH_3)_3SiO$ or $(CH_3CH_2)_3SiO$ or mixtures thereof, such as $(CH_3CH_2)(CH_3)_2SiO$.

It is believed by the inventor that such compounds are new and novel.

As indicated above, this invention, in another aspect, deals with a new and novel process for preparing the inventive organosilicon compounds. Thus, a further aspect of this invention is a method for preparing a compound which comprises (I) contacting 8-hydroxyquinoline with an allylhalide in the presence of an anhydrous base and a solvent for a period of time sufficient to react essentially all of the allylhalide with the 8-hydroxyquinoline; (II) distilling the product from (I) to remove any solvent and unreacted reactants from the reaction mixture; (III) heating the residue product from (II) in an inert atmosphere until essentially all of the residue product is rearranged to form allyl containing, 8-hydroxyquinoline; (IV) treating the rearranged reaction product from (III) with a silylating agent selected from a group consisting of $(R''_3Si)_2NH$, $R''_3SiCl$ and $R''_3SiOR'''$ wherein R'' is an alkyl group containing 1 or 2 carbon atoms and R''' is an alkyl radical containing 1 to 4 carbon atoms; (V) reacting the reaction product from (IV) with $(R''''O)_3SiH$, wherein R'''' is an alkyl radical containing 1–4 carbon atoms, in the presence of a hydrosilation catalyst, whereby a compound is formed of the formula

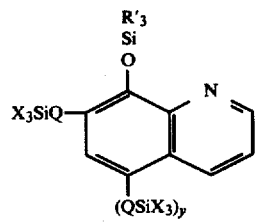

wherein X is an alkoxy radical containing 1–4 carbon atoms; Q is

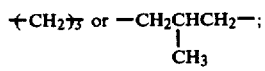

y has a value of 0 or 1; R' is an alkyl radical containing 1 or 2 carbon atoms.

The method consists of preparing an allyloxy derivative of the quinoline compounds; rearranging such allyloxy derivative to the allyl derivative of hydroxyquinoline; blocking the hydroxy group on the benzene ring because it interferes with the alkoxysilane addition; adding the alkoxysilanes by hydrosilation using hydrosilation catalysts and, if desired, hydrolyzing the final product in a lower aliphatic alcohol to obtain the hydroxyquinoline form.

In such a method, the 8-hydroxyquinoline is first reacted with an allylhalide using an anhydrous base as a catalyst. The object of the reaction is to prepare an allyloxyquinoline compound. Any allylhalide such as allylbromide, allylchloride or methallylbromide can be used in this invention but the inventor prefers allylbromide. Allylchloride requires somewhat higher temperatures and longer reaction times and is less preferred. An anhydrous base, for example KOH, NaOH or $Na_2CO_3$ should be used to enhance the reaction:

Solvents are generally used for this reaction and preferred solvents are lower aliphatic alcohols. Especially preferred are methanol and ethanol. Generally mole equivalents of the allylhalide and the 8-hydroxyquinoline are used. The reaction is usually carried out at a gentle reflux and therefore, the solvent used will dictate at what temperature the reaction will be carried out. These reactions can be refluxed for as little as one-half hour but it is generally beneficial to reflux the reaction for 2–4 hours. The appearance of Br— in the reaction mixture is indicative of the reaction taking place. A simple standardized $AgNo_3$ titration for Br— can be used to monitor the reaction. When one equivalent of Br— has appeared, the reaction is essentially complete. In this type of reaction, halide salts are formed as a by-product and these must be filtered from the reaction mixture. Several rinses of the solids with fresh solvent ensures that the reaction product is freed from the by-produced solids.

The filtrate is then stripped to remove solvents and the residue product is heated to an elevated temperature in an inert atmosphere such as nitrogen or argon. The elevated temperatures result in a Claisen-type rearrangement of the molecule to the 7-allyl substituted, 8-hydroxyquinoline. Such temperatures are usually in the range of 150° C. to 250° C. For purposes of this invention 180° C. for 6 hours or less for the monosubstituted quinoline, and 200° C. for 5 hours or less for the bis compound, is preferred.

If the bis compound is desired, the reaction sequence should be interrupted at this point and the 7-allyl-8-hydroxyquinoline should be treated with an additional equivalent of allylhalide as was done at the outset of the reaction sequence. The reaction with additional allylhalide should be carried out the same as the original reaction, using anhydrous base and about a mole equivalent of the allylhalide. This results in 7-allyl-8-allyloxyquinoline which, upon subsequent heating, rearranges to 5,7-(diallyl)-8-hydroxyquinoline.

In order to prepare the alkoxy-functional organosilicon compounds, one has to add the appropriate trialkoxysilane to the allyl substituted quinoline. This reaction is known as a hydrosilation reaction. Such reactions are well-known in the art. Generally, platinum or palladium, either supported or unsupported, is used as the hydrosilation catalyst. In order to prevent interference in the hydrosilation reaction, the hydroxy group on the allyl substituted quinoline has to be blocked. A most effective manner of blocking the hydroxyl group is through the use of silylating agents. Such agents are known in the art and for purposes of this invention, the preferred agents are {(CH₃)₃Si}₂NH, (CH₃)₃SiCl or (CH₃)₃SiOR where R is an alkyl radical of 1–4 carbon atoms.

Generally, the hexamethyldisilazane, in conjunction with a trace amount of the trimethylchlorosilane, is the best method of silylating the hydroxyquinoline of this invention. The silylating agents and the 7-allyl-8-hydroxyquinoline are mixed together and warmed (40°-60° C.) for several hours. Generally, 4–6 hours is sufficient to affect the reaction. The excess silazane, if any, and solvents are then removed, preferably under vacuum, and the residue is heated to give the trialkylsiloxy-derivative i.e.

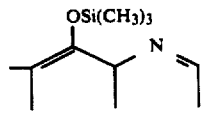

It is when this reactive carbinol is "capped" by the trialkylsiloxy group that the next step in the reaction sequence can be carried out.

In order to carry out the hydrosilation reaction, the reaction must be carried out in solvent and a hydrosilation catalyst must be used. Any hydrosilation catalyst is effective herein but preferred is platinum. Especially preferred is chloroplatinic acid in a solvent solution. Generally, the reaction is carried out at elevated temperatures. Occasionally, the reaction has to be carried out at reflux temperatures. The time required to carry out this reaction can vary from several hours to several days depending on the reactants, solvents and catalyst utilized. After the reaction is complete, the solvents and any other low boiling materials are stripped away or the crude reaction product can be used as it is obtained depending on the end use of such a product.

If the product is to be utilized as the hydroxyquinoline, the trialkylsiloxy "capping" group has to be removed. This can be done by hydrolyzing the product. Hydrolysis, however will not only remove the trialkylsiloxy capping group but hydrolysis will also cause the removal of the alkoxy groups on silicon. If this alkoxy group removal is to be avoided so that just the trialkylsiloxy group is removed and the carbinol group is regenerated, the hydrolysis can be carried out using limited water and an alcohol solvent such as methanol or ethanol. Utilizing this limited hydrolysis, the compounds having the general formula

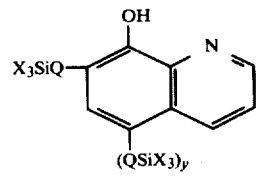

can be obtained.

For purposes of this invention, the crude product is generally used to treat the inorganic solid substrate and the water found on such substrates hydrolyzes the trialkylsiloxy and trialkoxy groups, in situ, during the substrate treatment.

Therefore, a third aspect of this invention is a method for preparing an immobilized chelating agent which comprises treating inorganic solid substrates with a silylating agent which is a compound of the formula

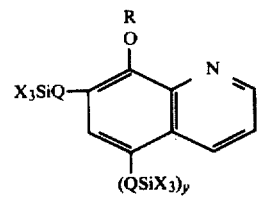

wherein X is an alkoxy radical containing 1–4 carbon atoms; Q is a

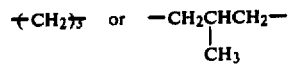

radical; y has a value of 0 or 1; R is hydrogen or an R′₃Si— radical wherein R′ is CH₃— or CH₃CH₂—.

The method is carried out by simply mixing the organosilicon compounds of this invention with the inorganic solid, usually in a water-insoluble solvent, and warming to a boiling stage for 1–2 hours. The concentration of the organosilicon compound in the treating solution is usually one-half to about five weight percent. The object is to cap all available hydroxyl groups on the surface with the organosilicon compound. As is obvious therefore, the inorganic solids that are useful in this invention are those which have hydroxyl groups on their surfaces. Further, such inorganic solids must be insoluble in water and solvents (although they should be dispersable therein) since applications for such materials within the scope of this invention are in various aqueous and solvent solutions. Examples of such inorganic solids are alumina, bentonite, sand, glass, silicas and silica gels.

It is preferred for purposes of this invention that the inorganic solid be finely divided. Finely divided for purposes of this invention means any particulate material having an average diameter of less than 10 mm. The treated inorganic solid is then filtered to remove the liquid portions and washed with fresh solvent and thereafter dried in an air circulating oven.

The dried chelating product is then ready for use and it can be stored in this manner. When used, the dried product is typically re-dispersed in the metal containing solution that is to be treated. Typically, this treatment is carried out at room temperature but it can also be carried out at higher temperatures. The pH of the treating solution may have to be adjusted in order to maximize the chelating capability of the product. A pH of 6.5–7.5 is considered to be advantageous for most applications.

The chelating substrate does not have infinite activity because the metal ions are removed from the metal ion solution relative to the amount of chelate available and this in turn is dependent on the amount of the chelate bound to the inorganic solid which is in turn dependent on the surface area of the inorganic solid and the number of hydroxyl groups available for coupling with the alkoxysilyl groups of the inventive organosilicon compounds. Further, the extent to which metal ion solution can be cleaned of metal ions is proportionate to the amount of treated substrate that comes in contact with metal ions. It therefore becomes advantageous in most applications to utilize, glass or plastic columns packed with the finely divided treated chelating substrate and pass the solution to be treated through such columns. However, batch treatments can be used with the chelating substrates of this invention.

When the substrate loses its activity for removing metals it may be discarded or the substrate may be reactivated by the use of mineral acid. One such method requires contacting the metal chelated substrate with an aqueous acid solution such as $HNO_3$, followed by separation of the aqueous acid solution from the substrate. The metal can then be recovered or discarded as desired.

Heavy metal ions contemplated within this invention are the transition elements (series 3b, 4b, 5b, 6b, 7b, 8b and 1b of the periodic table) and the zinc family (series 2b of the periodic table). Especially contemplated within the scope of this invention are the rare earth metal ions, the lanthanides and actinides. This invention is especially useful for removal of the more commonly used metals such as copper, platinum, nickel, gold, silver and iron.

The following examples are shown to illustrate the invention and are not intended to define the scope thereof.

EXAMPLE 1

Preparation of 7-allyl-8-hydroxyquinoline, a precursor compound

To a 250 ml, 3-necked, round-bottomed glass flask was added 16.8 gms (0.3 moles) of anhydrous KOH dissolved in 120 gms of 2B ethanol, 45 gms (0.3 moles) of 8-hydroxyquinoline and 36 gms (0.3 moles) of allylbromide. The reaction flask was equipped with a reflux condenser, thermometer and stirrer. With stirring, the mixture was heated for 2 hours at 80° C. (reflux). At the end of two hours, a sample of the reaction mixture was titrated with standardized $AgNO_3$ for bromide content and it was found that all of the allylbromide had reacted. The salts that were formed were removed by filtration and the salts were rinsed with additional 2B ethanol. The washings were combined with the filtrate.

The filtrate was then distilled to remove the ethanol whereby a small amount of solid material collected on the condenser. This material was isolated and found to be 8-hydroxyquinoline. Proton Nuclear Magnetic resonance analysis (H'NMR) showed

| type of Bond | suggested group | δ | proton ratio |
|---|---|---|---|
| multiple | pyridine | 8.64 | 1 |
| singlet | C—hydroxy | 8.37 | 1 |
| multiple | pyridine | 7.99 | 1 |
| singlet | pyridine + aromatic | 7.0–7.4 | 4 |

The remaining reaction product was distilled at 135°–150° C. at 2.5 mm of Hg. A gas-liquid chromatography (GLC) analysis of the distillate indicated two major peaks. The material was then heated at 180° C. under nitrogen purge for three hours. A GLC analysis showed only one peak which was believed to be 7-allyl-8-hydroxyquinoline.

The product was cooled to room temperature and recrystallized from methanol and water to yield about 20 gms of yellowish white flakes. An analysis showed $n_D^{25}$ of 1.61592 and a melting point of 42°–43° C.

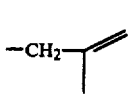

| type of Bond | suggested group | δ | proton ratio |
|---|---|---|---|
| singlet | hydroxy | 8.93 | 1 |
| multiple | pyridine | 8.30 | 1 |
| multiple | pyridine | 6.76 | 1 |
| multiple | pyridine + aromatic | 6.97 | 3 |
| multiple | —$CH_2$— | 6.00 | 1 |
| multiple | —$CH_2$= | 5.07 | 2 |
| multiple | —$CH_2$— | 3.55 | 2 |

Infra-red analysis showed both COH and $CH_2$=CH to be present.

EXAMPLE 2

Silylation of 7-allyl-8-hydroxyquinoline, a precursor compound

A one-ounce vial was loaded with 4.75 gms (0.026 moles) of 7-allyl-8-hydroxyquinoline in 10 ml. of dry toluene, 4.2 gms (0.026 moles) of hexamethyldisilazane and 2 drops of $(CH_3)_3SiCl$. The reaction was carried out at 40° C. for 6 hours while being monitored by GLC. A peak which eluted on the GLC column at a slightly lower temperature than the starting materials was observed. The excess toluene and silazane were removed under a vacuum strip at 40° C. and 1 mm Hg. An infra-red analysis showed the absence of the phenolic hydroxyl indicating that it had been capped with $(CH_3)_3Si$—. The pure compound has an $n_d^{25}$ of 1.5529.

EXAMPLE 3

Preparation of 7-trimethoxysilylpropyl-8-trimethyl-siloxyquinoline i.e.

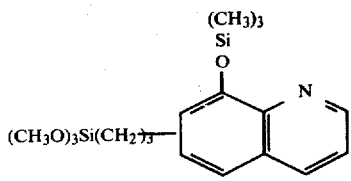

To a one-ounce glass vial containing 6.7 gms (0.026 moles) of 7-allyl-8-trimethylsiloxyquinoline was added 6.34 gms (0.052 moles) of trimethoxysilane and a trace of platinum catalyst ($H_2PtCl_6 \cdot 4H_2O$). Some bubbling occurred. The reaction was warmed at 40° C. for 8 hours during which time the reaction was monitored by GLC. A GLC after 3 days at 40° C. showed a small amount of the starting silane and a large product peak corresponding to

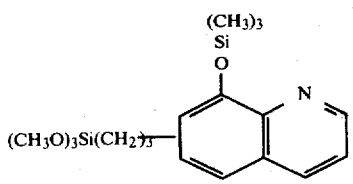

Analysis showed $n_d^{25} = 1.525$. Infra-red analysis showed the disappearance of the C=C peak. H'NMR:

| Group | δ | proton ratio |
|---|---|---|
|  | 6.00 and 7.80 | 1.0 |
| $CH_3O$ | 3.51 | 3.0 |
| $-Si(CH_2)_3$ |  | 1.7 |
| $CH_3Si\equiv$ |  | 1.6 |

EXAMPLE 4

Preparation of bis-(5,7-trimethoxysilylpropyl)-8-trimethylsiloxyquinoline i.e.

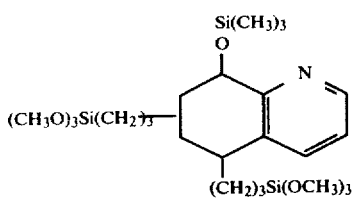

In a manner similar to that of Example 3, 25 gms of 8-hydroxyquinoline; 9.3 gms of anhydrous KOH in 100 ml of 2B ethanol and 21 gms of allylbromide were warmed to about 40° C. for about 2 hours. The product formed was filtered to remove the solids and the solids were rinsed twice with methanol and the rinses were added to the filtrate. The filtrate was stripped under vacuum to remove the solvent and then it was heated to 200° C. briefly to rearrange the allylether to the 7-allyl-8-hydroxyquinone. This material was cooled and 9.3 gms of KOH and 21 gms of allylbromide in 100 ml of ethanol was added to it and the mixture was warmed for 1 hour. The material was then cooled and filtered. This filtrate was titrated for $Br^-$ and there was found 0.17 equivalents of $Br^-$ indicating the majority of the allylbromide had reacted. The filtrate was stripped under vacuum and then heated to 200° C. This material was then cooled and 10 gms of {$(CH_3)_3Si$}$_2NH$ and 3 drops of $(CH_3)_3SiCl$ was added to silylate the carbonoxy group on the benzene ring. It was then stripped to 120° C. at 10 mm to remove any volatile materials. To this reaction product was added 3 drops of 1% chloroplatinic acid in isopropanol and 50 gms of $(CH_3O)_3SiH$ and this mixture was warmed to 110° C. for 2 hours. It was then stripped to remove excess $(CH_3O)_3SiH$, cooled, and diluted with 105 gms of dry toluene. The material was dark amber in color and clear.

EXAMPLE 5

The preparation of silica treated with a chelating silane

A silica gel (Davison-Grade 62, manufactured by Davison, a division of W. R. grace Co., 10 E. Baltimore St., Baltimore, MD) was used in the following test. This grade 62 silica has a pore volume of 1.15 cc/gm; average pore diameter of 140 Angstroms; surface area of 340 $m^2$/gm and a mesh size of 60-200 (U.S. Standard mesh).

Small portions of the silica gel and the silane

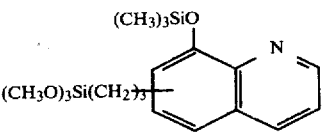

were mixed together and warmed to a gentle boil for 1 hour. The silanes were used as 2% solutions in toluene. The treated silica was recovered by filtration and washed by fresh toluene and then dried for 2 hours in a 60° C. air-convection oven.

Five gram portions of treated silica were mixed with 50 ml of 1% $Cu^{++}$ (chloride) solution and adjusted to pH 7 with ammonia. After mixing for 15 minutes, the treated silica was filtered and washed 10 times with deionized water. The washed silica was then stirred with 30 ml. of 1% $HNO_3$ for 30 minutes. A portion of the $HNO_3$ was analyzed for $Cu^{++}$ by atomic absorption. The acid eluted silica was rinsed with water and stored under water, as shown in the table below. This was one cycle. The treated silica was then recycled with more copper solution. Cycles were repeated after 1, 4 and 45 days storage in water. Copper capacity is reported as ppm $Cu^{++}$ in the 30 ml nitric acid solution: Copper concentration of 1000 ppm is equivalent to a capacity of 0.1 milliequivalents of copper per gram of silica. Copper capacities are shown in Table I (Samples A–C).

Reference sample A is the untreated silica. The prior art polyamino silane is shown as reference sample B. Note that the initial chelating capacity of B was 1000 but after two and then three cycles, the capacity dropped off dramatically whereas sample (C), the material of this invention, maintains its chelating capacity for three full cycles. A fourth cycle (after 45 days under water) on sample (C) showed the chelating capacity to still be 650.

EXAMPLE 6

Ten grams of Davison 62 silica gel was warmed with 50 ml of 2% solids silane in toluene to reflux for 15 minutes. The treated silica was filtered, rinsed on the filter with fresh toluene and dried for two hours in a 60° C. convection oven. The silane was that prepared in Example 4. The copper capacity of this treated silica was determined as in Example 5.

See Table I (Samples A, B and D).

The inventive material D, does not have the original capacity that the inventive compound C has but it can be observed that compound C has the same type of enhanced prolonged activity as does compound C when compared to compound B.

EXAMPLE 7

When the compound of Example 3 is hydrolyzed in the presence of methanol as the solvent, the alkoxy groups on the silicon atom remain and the compound

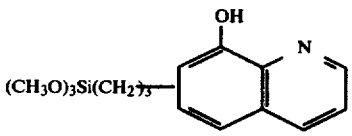

is obtained. This material, when used as a treatment for silica as was done in Example 5, gives essentially equivalent chelating results as shown in Example 5.

That which is claimed is:

1. A compound of the formula

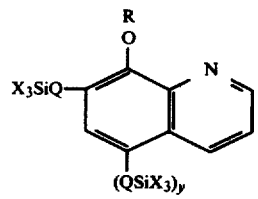

wherein

X is an alkoxy radical containing 1-4 carbon atoms;
Q is a

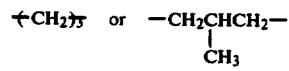

radical;
y has a value of 0 or 1;
R is hydrogen or an $R'_3Si$— radical wherein R' is $CH_3$— or $CH_3CH_2$—.

2. A compound as claimed in claim 1 wherein y is zero.
3. A compound as claimed in claim 2 wherein R is hydrogen and X is methoxy.
4. A compound as claimed in claim 2 wherein R is $R'_3Si$.
5. A compound as claimed in claim 4 wherein R' is methyl.
6. A compound as claimed in claim 1 wherein y is one.
7. A compound as claimed in claim 6 wherein R is hydrogen and X is methoxy.
8. A compound as claimed in claim 6 wherein R is $R'_3Si$.
9. A compound as claimed in claim 8 wherein R' is methyl.
10. A method of preparing a compound which comprises
  (I) contacting 8-hydroxyquinoline with an allylhalide in the presence of an anhydrous base and a solvent

TABLE I

| | Copper Capacity of Silylated Silica Gel | | | |
| | $Cu^{++}$ in $HNO_3$ acid rinse (ppm) | | | |
| treatment on silica gel | 1st cycle | 2nd cycle 1 day later | 3rd cycle 4 days later | % retention from 3rd cycle |
| --- | --- | --- | --- | --- |
| A. Untreated Silica | 114 | 50 | 51 | — |
| B. $O_{3/2}Si(CH_2)_3N(CH_2)_2NH_2$ $\phantom{O_{3/2}Si(CH_2)_3N}H$ | 1000 | 225 | 108 | 10.8 |
| C. [structure: $O_{3/2}Si(CH_2)_3$-substituted 8-hydroxyquinoline] | 920 | 910 | 920 | 100 |
| D. [structure: $O_{3/2}Si(CH_2)_3$-substituted 8-hydroxyquinoline with $(CH_2)_3SiO_{3/2}$ group] | 680 | 650 | 450 | 66 | for a period of time sufficient to react essentially all of the allylhalide with the 8-hydroxyquinoline;

(II) distilling the product from (I) to remove any solvent and unreacted reactants from the reaction mixture;

(III) heating the residue product from (II) in an inert atmosphere until essentially all of the residue product is rearranged to form allyl containing, 8-hydroxyquinoline;

(IV) treating the rearranged reaction product from (III) with a silylating agent selected from a group consisting of $(R''_3Si)_2NH$, $R''_3SiCl$ and $R''_3SiOR'''$ wherein $R''$ is an alkyl group containing 1 or 2 carbon atoms and $R'''$ is an alkyl radical containing 1 to 4 carbon atoms;

(V) reacting the reaction product from (IV) with $(R''''O)_3SiH$, wherein $R''''$ is an alkyl radical containing 1–4 carbon atoms in the presence of a hydrosilation catalyst, whereby a compound is formed of the formula

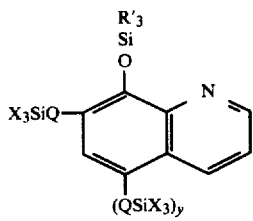

wherein
X is an alkoxy radical containing 1–4 carbon atoms;
Q is

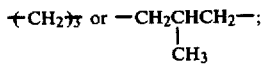

y has a value of 0 or 1;
R' is an alkyl radical containing 1 or 2 carbon atoms.

11. The method of claim 10 wherein the reaction product from step V is further contacted with moisture in the presence of a lower aliphatic alcohol to obtain the compound

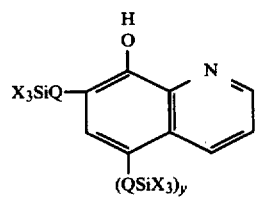

12. The method of claim 11 wherein the lower aliphatic alcohol is $CH_3OH$.

13. A method as claimed in claim 10, wherein in (I) the allylhalide is allylbromide; in (IV) the silylating agent is $(R''_3Si)_2NH$; in (V), $(R''''O)_3SiH$ is $(CH_3O)_3SiH$ and the catalyst is platinum.

* * * * *